United States Patent
Sato et al.

(10) Patent No.: US 10,349,886 B2
(45) Date of Patent: Jul. 16, 2019

(54) ARTERY VISUALIZATION DEVICE AND ARTERY IMAGING DEVICE

(71) Applicant: National University Corporation Kochi University, Kochi (JP)

(72) Inventors: Takayuki Sato, Kochi (JP); Tatsumi Ike, Kochi (JP)

(73) Assignee: National University Corporation Kochi University, Kochi (JP)

( * ) Notice: Subject to any disclaimer, the term of this patent is extended or adjusted under 35 U.S.C. 154(b) by 786 days.

(21) Appl. No.: 14/403,632

(22) PCT Filed: May 28, 2013

(86) PCT No.: PCT/JP2013/064763
§ 371 (c)(1),
(2) Date: Nov. 25, 2014

(87) PCT Pub. No.: WO2013/180126
PCT Pub. Date: Dec. 5, 2013

(65) Prior Publication Data
US 2015/0133791 A1    May 14, 2015

(30) Foreign Application Priority Data
May 29, 2012  (JP) ................................ 2012-121700

(51) Int. Cl.
*A61B 5/00*        (2006.01)
*A61B 90/13*       (2016.01)
(Continued)

(52) U.S. Cl.
CPC ............ *A61B 5/489* (2013.01); *A61B 5/0075* (2013.01); *A61B 5/0077* (2013.01);
(Continued)

(58) Field of Classification Search
CPC ......... A61B 5/00; A61B 5/702; A61B 5/6824; A61B 5/0086; A61B 5/0084; A61B 5/0059
See application file for complete search history.

(56) References Cited

U.S. PATENT DOCUMENTS 6,191,599 B1 *  2/2001  Stevens .............. G01R 31/2862
                                                        324/750.07
6,424,858 B1    7/2002  Williams
(Continued)

FOREIGN PATENT DOCUMENTS

EP        2007273 A     12/2008
EP        2289578 A1     3/2011
(Continued)

OTHER PUBLICATIONS

Official Notice of Reason for Refusal and English translation thereof, dated Oct. 6, 2015, received in Japanese Patent Application No. 2014-192946.
(Continued)

*Primary Examiner* — Tse W Chen
*Assistant Examiner* — Jason M Ip
(74) *Attorney, Agent, or Firm* — Nixon Peabody LLP; Thomas P. Pavelko

(57) ABSTRACT

[Problem] To provide an artery visualization device capable of very appropriately visualizing a to-be-punctured artery and an artery imaging device used for the artery visualization device.
[Solution] An artery visualization device (10) includes en irradiation unit (30) which irradiates the near-infrared light emitted from a light source (32) toward a back-side skin surface (22) at a visualization site (20) where a to-be-punctured artery (21) is running, a light guiding part (40) which encapsulates the light source and is pressed against the back-side skin surface and which is formed with a
(Continued)

material of transmitting the near-infrared light emitted from the light source and suppressing reflection of the near-infrared light on the surface of the back-side skin surface, an optical filter (50) which blocks visible light and transmits the near-infrared light passing through a front-side skin surface (23) at the visualization site, a camera (60) (an imaging unit) which receives the near-infrared light passing through the optical filter to capture an image of the visualization site (20), and a monitor (70) (a display unit) which displays the image captured by the camera.

18 Claims, 5 Drawing Sheets

(51) Int. Cl.
 *A61B 90/11* (2016.01)
 *A61M 5/42* (2006.01)
(52) U.S. Cl.
 CPC .......... *A61B 5/0086* (2013.01); *A61B 5/6824* (2013.01); *A61B 5/6843* (2013.01); *A61B 5/702* (2013.01); *A61B 5/742* (2013.01); *A61B 90/11* (2016.02); *A61B 90/13* (2016.02); *A61B 5/6831* (2013.01); *A61B 2562/185* (2013.01); *A61M 5/427* (2013.01)

(56) References Cited

U.S. PATENT DOCUMENTS

| | | | |
|---|---|---|---|
| 6,443,928 | B1 | 9/2002 | Francis |
| 2002/0026121 | A1* | 2/2002 | Kan ............... A61B 5/02116 600/500 |
| 2005/0143652 | A1 | 6/2005 | Sato |
| 2006/0095058 | A1 | 5/2006 | Sivan et al. |
| 2008/0039715 | A1 | 2/2008 | Wilson et al. |
| 2009/0005685 | A1* | 1/2009 | Nagae ............... A61B 5/0059 600/459 |
| 2009/0009595 | A1 | 1/2009 | Ishiwata et al. |
| 2010/0177182 | A1 | 7/2010 | Kagenow et al. |
| 2011/0009751 | A1 | 1/2011 | Mcguire, Jr. et al. |
| 2011/0092811 | A1 | 4/2011 | Yasui |
| 2012/0029366 | A1* | 2/2012 | Yokoyama ........... A61B 5/0225 600/490 |

FOREIGN PATENT DOCUMENTS

| | | |
|---|---|---|
| JP | 2004237051 A | 8/2004 |
| JP | 2005191748 A | 7/2005 |
| JP | 2008515586 A | 5/2008 |
| JP | 3144999 U | 9/2008 |
| JP | 2009532140 A | 9/2009 |
| JP | 2010148853 A | 7/2010 |
| JP | 2010528818 A | 8/2010 |
| JP | 2011200374 A | 10/2011 |
| KR | 20100135288 A | 12/2010 |
| WO | WO-2007115570 A1 | 10/2007 |
| WO | WO-2008154533 A1 | 12/2008 |
| WO | 2009125349 A2 | 10/2009 |
| WO | WO-2009154081 A1 | 12/2009 |

OTHER PUBLICATIONS

Extended European Search Report of foreign counterpart application EP13796430.0 dated Feb. 2, 2016.
International Preliminary Report on Patentability dated Dec. 4, 2014.
International Search Report dated Jul. 2, 2013.
International Preliminary Report on Patentability dated Apr. 1, 2014.
European Office Action for Application No. 13 796 430.0 dated Oct. 12, 2018.

* cited by examiner

ARTERY VISUALIZATION DEVICE AND ARTERY IMAGING DEVICE

CROSS-REFERENCE TO RELATED APPLICATIONS

This application is a National Phase tiling under 35 U.S.C. § 371 of PCT Patent Application Serial No. PCT/JP2013/064763 filed on May 28, 2013, which claims priority of Japanese Patent Application Serial No. 2012-121700 filed on May 29, 2012, the entire contents of which is hereby incorporated by reference.

TECHNICAL FIELD

The present invention relates to an artery visualization device and an artery imaging device.

BACKGROUND ART

In examination or treatment using a catheter, for example, in cardiac catheterization examination, an artery is punctured, a guide wire is inserted, and the catheter inserted. The to-be-punctured portion is a radial artery, a brachial artery, a femoral artery, or the like. With respect to the radial artery among these arteries, it is easy to secure rest of hemostasis after examination, and since actions of a patient do not need to be restrained, the radial artery is suitable as a to-be-punctured portion.

On the other hand, a high technique is required for the puncture of the radial artery. In general, the puncture of the radial artery is performed while estimating running of the radial artery by palpation. In the case where the puncture is difficult, the puncture may be sometimes performed by using ultrasonic diagnostic equipment. However, manipulation procedures accompanied with scanning a probe are complicated, and the ultrasonic diagnostic equipment is relatively expensive From such a clinical background, a technique of visualizing various arteries with a simple configuration and a relatively low cost, particularly, a technique of visualizing a radical artery has been eagerly waited for.

By the way, it is known that near-infrared light has a high permeability with respect to a human tissue such as skin, fat, and muscle. A blood vessel visualization device utilizing a property in that hemoglobin in blood absorbs near-infrared light has been proposed (refer to Patent Literature 1). Patent Literature 1 discloses a technique of visualizing a blood vessel of a finger for the purpose of performing biometric authentication.

As commercialized blood vessel visualization devices using near-infrared light and a near-infrared camera, a blood vessel visualization device "VeinViewer" (registered trademark) produced by Christie Medical Holdings Inc., a non-contact vein visualization device "StatVein" (registered trademark) produced by Techno Medica Co., Ltd., and the like are known.

CITATION LIST

Patent Literatures

Patent Literature JP-2005-191748 A

SUMMARY OF INVENTION

Technical Problem

However, the blood vessel visualization device disclosed in Patent Literature 1 is considered to have the main object of biometric authentication, and thus, the device is not contrived for the purpose of arterial puncture. There is no description of anatomical characteristics of to-be-punctured blood vessels, and finger is mentioned only as an objective living body (refer to FIGS. 2 and 11 of Patent Literature 1). However, the artery of the finger is thin, and the puncture for an examination and a treatment using catheter is not performed. In addition, in comparison with a radial artery or a brachial artery, the artery of the finger is running at the shallow sites beneath the skin (at the sites in the depth of 2 to 3 mm beneath the skin). Since the artery of the finger is not surrounded by bones, it is easy to irradiate transmission light. In addition, although the near-infrared light emitted from a light source propagates air to be irradiated on the living body, light reflected on the surface of the skin is not considered.

The above-described commercialized blood vessel visualization device ("VeinViewer" (registered trademark), "StatVein" (registered trademark), and the like) are merely devices capable of visual visualizing veins located within a depth of 2 to 3 mm beneath the skin.

Like this, devices for visualizing to-be-punctured arteries located in the depth of 5 to 10 mm beneath the skin, for example, devices for visualizing radial arteries or the like surrounded by bones have not been proposed.

Therefore, an object of the present invention is to provide an artery visualization device capable of very appropriately visualizing a to-be-punctured artery and an artery imaging device used for the artery visualization device.

Means for Solving Problem

In order to achieve the above object, according to an aspect of the present invention, there is provided an artery visualization device including:

an irradiation unit which includes a light source emitting near-infrared light and irradiates the near-infrared light emitted from the light source toward a back-side skin surface at a visualization site where a to-be-punctured artery is running, a light guiding part which encapsulates the light source and is pressed against the back-side skin surface and which is formed with a material of transmitting the near-infrared light emitted from the light source and suppressing reflection of the near-infrared light on a surface of the back-side skin surface, an optical filter which blocks visible light and transmits the near-infrared right passing through a front-side skin surface at the visualization site, an imaging unit which receives the near-infrared light passing through the optical filter to capture an image of the visualization site, and a display unit which displays the image captured by the imaging unit.

In addition, in order to achieve the above object, according to another aspect of the present invention, there is provided an artery imaging device used for the artery visualization device according to the present invention, and the artery imaging device includes the irradiation unit, the light guiding part, the optical filter, and imaging unit.

Advantageous Effect of the Invention

In the artery visualization device according to the present invention, the near-infrared light is incident from the back-side skin surface at the visualization site where the to-be-punctured artery is running, the absorption image of the near-infrared light absorbed by the artery is formed in the imaging unit which captures an image from the side of the back-side skin surface at the visualization site. Since the near-infrared light is incident on the back-side skin surface, the reflection of the near-infrared light does not occur on the surface of the front-side skin surface. Since the light guiding part which encapsulates the light source and is pressed against the back-side skin surface is formed with a material transmitting the near-infrared light and suppressing the reflection of the near-infrared light on the surface of the back-side skin surface, it is possible to allow the near-infrared light to be efficiently incident on the back-side skin surface at the visualization site. By pressing the light guiding part against the back-side skin surface, a capillary network of the skin is collapsed, so that the absorption of the near-infrared light in the skin portion on which the near-infrared light is inc dent is suppressed. As a result, it is possible to very appropriately visualize the to-be-punctured artery.

According to an artery imaging device, an artery visualization device capable of very appropriately visualizing the to-be-punctured artery may be configured by connecting to an existing display unit, so that the artery imaging device has advantages in terms of costs.

DESCRIPTION OF EMBODIMENTS

Figure 1:
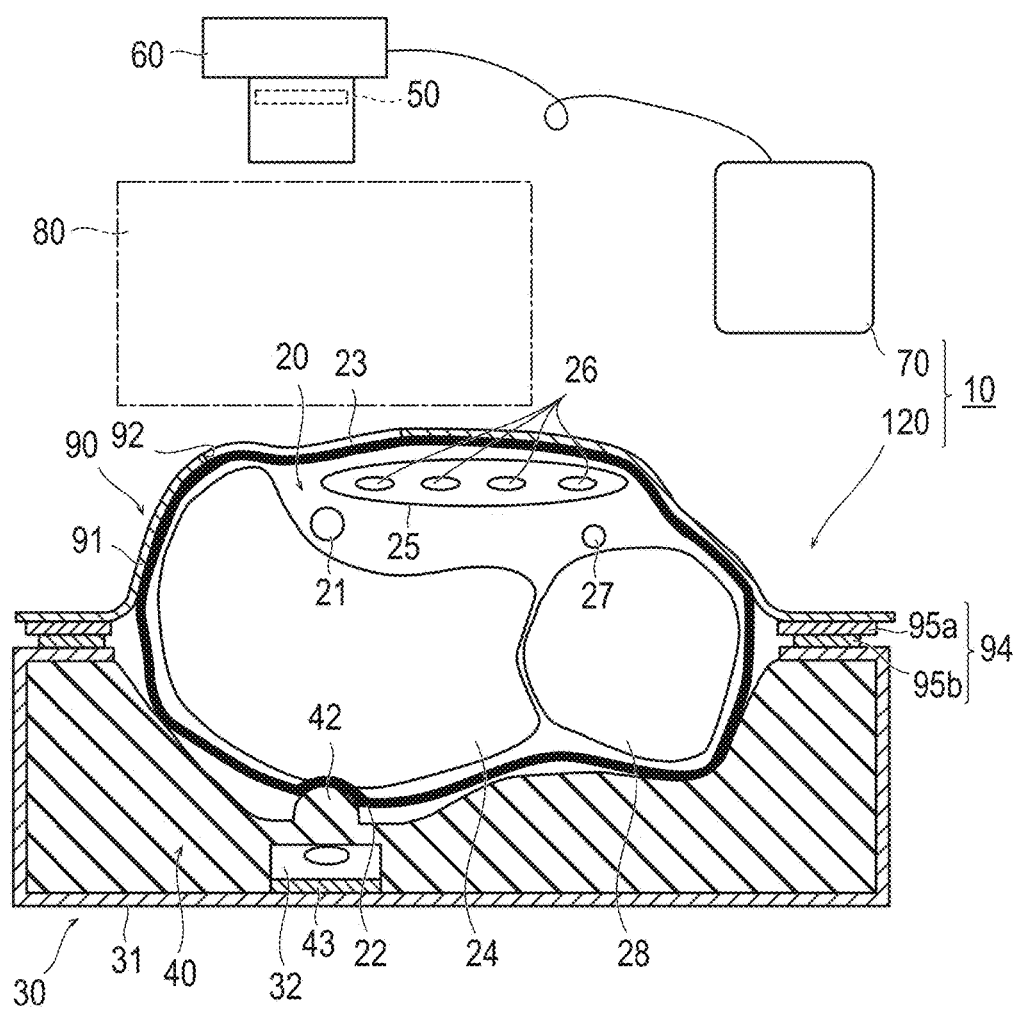
FIG. 1 is a cross-sectional diagram illustrating an artery visualization device according to a first embodiment.

Near-infrared light having a high bio-permeability and a wavelength which is absorbed by hemoglobin is preferably used as irradiation light on a visualization site where arteries are running. An absorption coefficient of the oxygenated hemoglobin flowing in the arteries has a wavelength dependency. In the near-infrared wavelength range having a high bio-permeability, the absorption coefficient has a maximum in a range of 850 nm to 930 nm (refer to http://www.frontech.fujitsu.com/services/products/palmsecure/what/interview/).

Epidermis located in the outermost layer of the skin reflects visible light and near-infrared light. Even in the case of the near-infrared light having a high bio-permeability, 80% of the irradiation light is reflected by the epidermis, and thus, about 10% of the light reaches a site in the depth of 3 mm beneath the skin (refer to Yoshihisa Aizu, "Skin Tissue Multilayer Structure Modeling, Journal of Japan Society of Mechanical Engineers, 2011. 7, vol. 114, no. 1112, 541 pages).

In general, puncture which is performed for the purpose of catheterization examination or invasive arterial pressure measurement is performed on a radial artery or a brachial artery. Therefore, in the visualization device for artery puncture, anatomical characteristics of the applied artery need to be considered.

The radial artery or the brachial artery is surrounded by bone tissues and is running in the depth of 5 to 10 mm beneath the to-be-punctured skin surface. In order to visualize the artery having such anatomical characteristics, the near-infrared light needs to be efficiently incident on the site where the artery is running, so that the near-infrared light needs to be emitted from the to-be-punctured skin surface.

In order to depict a near-infrared absorption image of the artery running in the depth of 5 to 10 mm beneath the skin, the near-infrared light needs not be irradiated on the surface of the skin of the to-be-punctured portion. This is because the reflected near-infrared light invalidates the absorption image by the artery.

The inventors of the present application insensitively studied based on the above-described findings, and as a result, achieved the technique for visualizing the radial artery and the brachial artery for the purpose of the puncture thereof.

Hereinafter, embodiments of the present invention will be described with reference to the attached drawings. In addition, in the description of the drawings, the same components are denoted by the same reference numerals, and the redundant description is omitted. Dimensional ratios in the drawings are exaggerated for the convenience of explanation, and thus, the ratios are different from actual ratios.

First Embodiment

Figure 2:
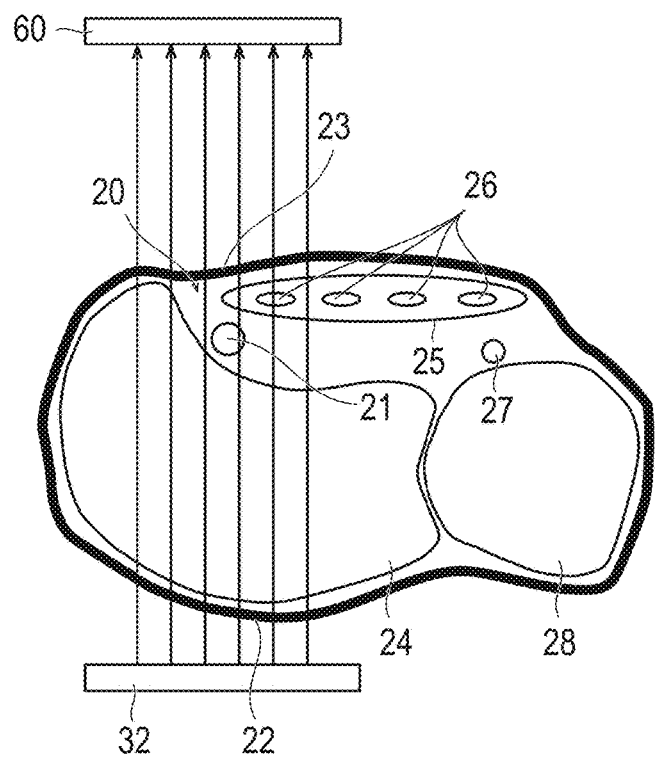
FIG. 2 is schematic cross-sectional diagram illustrating a manner of incidence of near-infrared into a living body.
Figure 3:
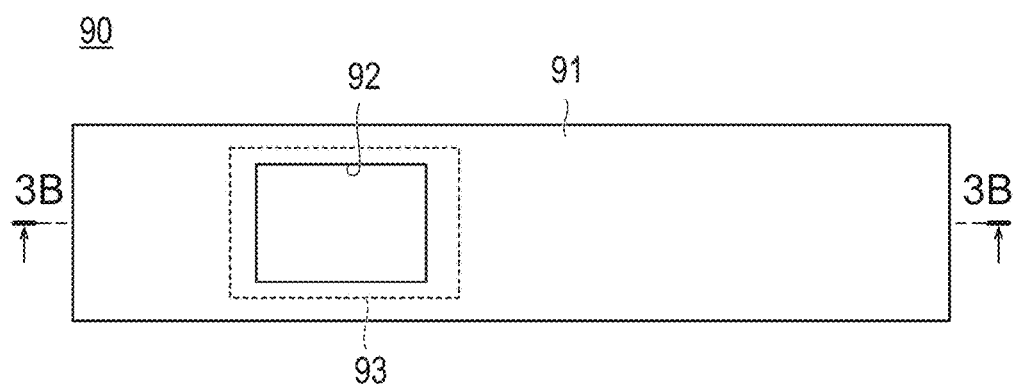
FIG. 3(A) is a front diagram illustrating development of a light shielding member illustrated in FIG. 1.
FIG. 3(B) is a cross-sectional diagram taken along line 3B-3B of FIG. 3(A).
Figure 3:
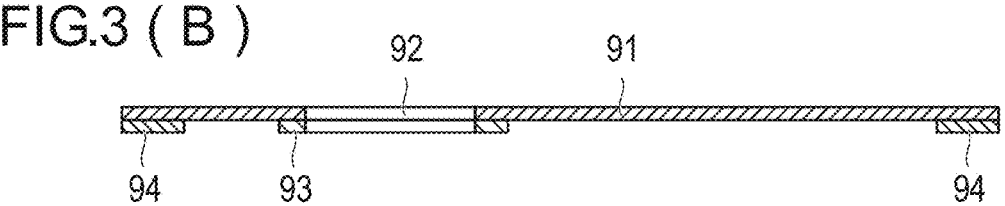

FIG. 1 is a cross-sectional diagram illustrating an artery visualization device 10 according to a first embodiment, and FIG. 2 is a schematic cross-sectional diagram illustrating a manner of incidence of near-infrared light into a living body. In addition, FIG. 3(A) is front diagram illustrating development of a light shielding member 90 illustrated in FIG. 1, and FIG. 3(B) is a cross-sectional diagram taken along line 3B-3B of FIG. 3(A).

As described in brief with reference to FIG. 1, the artery visualization device 10 according to the first embodiment is configured to include an irradiation unit 30 which includes a light source 32 emitting near-infrared light and irradiates the near-infrared light emitted from the light source 32 toward a back-side skin surface 22 at a visualization site 20 where a to-be-punctured artery 21 is running, a light guiding part 40 which encapsulates the light source 32 and is pressed against the back-side skin surface 22 and which is formed with a material of transmitting the near-infrared light emitted from the light source 32 and suppressing reflection of the near-infrared light on the surface of the back-side skin surface 22, an optical filter 50 which blocks visible light and transmits the near-infrared light passing through a front-side skin surface 23 at the visualization site 20, a camera 60 (corresponding to an imaging unit) which receives the near-infrared light passing through the optical filter 50 to capture an image of the visualization site 20, and a monitor 70 (corresponding to a display unit) which displays the image captured by the camera 60. In the artery visualization device 10, the front-side skin surface 23 and the imaging unit 60 are arranged so as to be separated from each other, and a work space 80 where the puncture is performed is installed between the front-side skin surface 23 and the imaging unit 60, Hereinafter, the artery visualization device 10 according to the first embodiment will be described in detail.

The illustrated visualization site 20 is, for example, a wrist portion where a radial artery as the to-be-punctured artery 21 is running. A hand is stretched to a side of the body, and the palm is directed upwards. The radial artery 21 is located in the depth of 5 to 10 mm beneath the skin and is surrounded by a radius 24, a carpal tunnel 25, a flexor tendon 26, and the like. In the figure, reference numeral 27 denotes an ulnar artery, and reference numeral 28 denotes an ulna.

The radiation unit 30 is configured to include a chassis 31 which is formed in a substantially hollow box shape and a light source 32 which is arranged inside the chassis 31 to emit the near-infrared light. The chassis 31 is formed with a metal material such as aluminum which does not transmit the near-infrared light. The visualization site 20 is placed from the upper surface side of the chassis 31. The near-infrared light emitted from the light source 32 is irradiated toward the back-side skin surface 22 at the visualization site 20. As the light source 32, for example, an LED or the like emitting the near-infrared light may be used. The irradiated near-infrared light is preferably in a wavelength range of 840 to 950 nm. This is because the near-infrared light in the wavelength range of less than 840 nm is hard to transmit the visualization site 20 and the near-infrared light having a long wavelength exceeding the wavelength of 950 cm is hard to transmit due to absorption by water inside the living body.

The irradiated near-infrared light is more preferably in a wavelength range of 850 to 930 nm. Since the absorption coefficient of the oxygenated hemoglobin flowing in the artery has a maximum in the wavelength range of 850 to 930 nm, transmission light of which signal intensity is decreased due to the artery 21 may be obtained. As a result, a difference in contrast between the transmission light passing through the artery 21 and the transmission light passing through peripheral tissues occurs, and thus, it is easy to visually recognize the artery.

As illustrated in FIG. 2, as the manner of incidence of the near-infrared light into the living body, a transmission manner using pseudo-parallel light is preferred. On an imaging plane, a transmission light image of the transmission light passing through the living body and absorption image of the light absorbed by the artery 21 are formed. Therefore, preferably, the transmission light is incident vertically on the imaging plane.

Even the near-infrared light having a high bio-permeability is easily reflected by the epidermis located in the outermost layer of the skin. In order to capture a clear image of the visualization site 20 by using the near-infrared light, it is necessary to suppress the reflection of the near-infrared light on the surface of the back-side skin surface 22. Therefore, the light guiding part 40 which encapsulates the light source 32 and is pressed against the back-side skin surface 22 as arranged between the light source 32 and the visualization site 20. The light guiding part 40 is formed with a material which transmits the near-infrared light emitted from the light source 32 and suppresses the reflection of the near-infrared light on the surface of the back-side skin surface 22. By the light guiding part 40, the near-infrared light is guided from the light source 32 to the back-side skin surface 22, and the reflection of the near-infrared light on the surface of the skin surface 22 is suppressed. As a result, the near-infrared light may be efficiently incident on the back-side skin surface 22 at the visualization site 20. In addition, since the near infrared light is incident on the back-side skin surface 22, the reflection of the near-infrared light does not occur on the surface of the front-side skin surface 23.

As a material for forming the light guiding part 40, a material having a high transmittance with respect to the near-infrared light is preferred, which is obvious in terms of the transmission of the near-infrared light from the light source 32 to the back-side skin surface 22. In addition, in terms of the suppression of the reflection of the near-infrared light on the surface of the skin surface 22, as a material for forming the light guiding part 40, a material having a refractive index close to the refractive index of the living body is preferred. Preferably, the refractive index of the light guiding part 40 is in a range of from the refractive index of water of 1.33, a large amount of which is contained in the living body, to the refractive index of collagen of 1.44, a large amount of which is contained in the living body.

As an example of the material for forming the light guiding part 40, a silicon rubber having a high transmittance with respect to the near-infrared light and a refractive index close to that of the living body may be exemplified, and the refractive index is in a range of 1.33 to 1.44. Due to the light guiding part 40 formed with the forming material, the near-infrared light may be efficiently incident on the back-side skin surface 22 at the visualization site 20.

Preferably, ointment or cream having a high transmittance with respect to the near-infrared light is applied on the surface of the light guiding part 40 which is pressed against the back-side skin surface 22. This is because the reflection of the near-infrared light on the surface of the back-side skin surface 22 may be further suppressed.

By pressing the light guiding part 40 against the back-side skin surface 22, the back-side skin surface 22 is pressed, so that a capillary network of the skin is collapsed. Therefore, the absorption of the near-infrared light at the skin portion on which the near-infrared light is incident may be suppressed. As a result, it is possible to efficiently irradiate the near-infrared light on the artery 21 located at a position deeper than the capillary network, so that it is possible to more clearly visualize the artery 21.

Preferably, a pressing portion 42 which protrudes toward the back-side skin surface 22 to press the back-side skin surface 22 is formed in the light guiding part 40. This is because the capillary network of the skin is easily collapsed by locally pressing the back-side skin surface 22 by using the pressing portion 42. Accordingly, it is possible further suppress the absorption of the near-infrared light in the skin portion on which the near-infrared light is incident, so that it possible to more clearly visualize the artery 21. If the shape of the pressing portion 42 is a shape of capable of easily collapsing the capillary network of the skin by pressing the back-side surface 22, the shape of the pressing portion 42 is not particularly limited. As illustrated, for example, a hemispherical shape may be exemplified. In addition, besides a shape having one convex portion, the pressing portion 42 may have a shape having a plurality of convex portions.

The pressure of pressing the light guiding part 40 against the back-side skin surface 22 is preferably in a range of 20 to 40 mmHg. This is because, by pressing the light guiding part 40 in a pressure range of 20 to 40 mmHg, the back-side skin surface 22 is pressed to collapse the capillary network of the skin, so that the absorption of the near-infrared light the skin portion on which the near-infrared light is incident suppressed.

A pressure sensor 43 is arranged between the back surface side of the light source 32 and the chassis 31. A contact pressure of pressing the light guiding part 40 against the back-side skin surface 22 is detected by the pressure sensor 43. A pressure detection method of the pressure sensor 43 is not particularly limited. For example, a pressure sensor using a method of detecting the pressure by reading out as a voltage signal, a change in electrical resistance caused by deflection of a diaphragm due to the external pressure and distortion of a piezoresistive element formed on the diaphragm may be applied. Since the deflection amount of the diaphragm is directly recognized as a change in electrical resistance of the piezoresistive element, there are a large number of the pressure sensors using the method, which have a simple element structure and are miniaturized. The contact pressure detected by the pressure sensor is displayed on the monitor 70 by using numerical values, indicator bars, or the like. By adjusting the force of pressing the visualization site 20 against the light guiding part 40 while checking the display, it is possible to regulate the contact pressure between the back-side skin surface 22 and the light guiding part 40 in a range of 20 to 40 mmHg.

The optical filter 50 may be inserted between an imaging element and a lens in the camera 60 or arranged in front of the camera 60. In order to visualize the artery 21 located at the position in the depth of 5 to 10 mm beneath the skin, it is preferable that components having a wavelength shorter than 840 nm be blocked.

As the camera 60, a CCD camera, a CMOS camera, or the like for the near-infrared light which images the near-infrared light passing through the visualization site 20 and the optical filter 50 is applied. The CCD camera is a camera configured with a charge coupled device (CCD) element, and the CMOS camera is a camera using a complementary metal oxide semiconductor (CMOS). Data acquired by the near-infrared light COD camera or the like are subject to image processes such as a noise process, an edge process, and a contrast enhancement process and an image analysis to be converted into data for an image which is to be displayed on the monitor 70.

If the monitor 70 is able to display the image captured by the camera 60, the monitor 70 is not particularly limited. A desk-top display may be used, and a head-mounted display may also be used. The displayed image may be any one of monochrome and color images. Medical persons such as operators may accurately recognize the position and direction of the running artery 21 by viewing the image of the artery 21 displayed on the monitor 70.

Since the artery visualization device 10 according to the embodiment is contrived for the purpose of easily performing the puncture of the artery 21, the skin at the to-be-punctured portion needs to be opened so as to perform the puncture. Therefore, the front-side skin surface 23 and the camera 60 are arranged so as to be separated from each other. As a result, the work space 80 where the puncture is performed is formed between the front-side skin surface 23 and the camera 50. The distance between the front-side skin surface 23 and the camera 60 may be set to be an appropriate distance in terms of securing the sufficient work space 80. As an example, the front-side skin surface 23 and the camera 60 are preferably arranged so as to be separated from each other by 20 centimeters or more.

The artery visualization device 10 is configured to further include a light shielding member 90 which covers the front-side skin surface 23. As illustrated in FIGS. 3(A) and 3(B), a light shielding portion 91 formed with a material of blocking the near-infrared light and an observation window 92 opened for imaging the visualization site 20 are installed in the light shielding member 90. The light shielding member 90 may be configured to cover the front-side skin surface 23 in the state that the observation window 92 is allowed to be located just over the radial artery 21. By covering with the light shielding member 90, the near-infrared light may be transmitted from only the to-be-punctured portion in the front-side skin surface 23, so that the visualization of the to-be-punctured artery 21 becomes reliable. As a material of blocking the near-infrared light, for example, a light-shielding rubber may be exemplified, but not limited thereto.

The light shielding member 90 is configured to include a protruding portion 93 which is arranged around the observation window 92 and protrudes from the light shielding portion 91. By allowing the protruding portion 93 to be in contact with the front-side skin surface 23, the near-infrared light passing through a site excluding the site which faces the observation window 92 in the front-side skin surface 23 is blocked from being mixed into the observation window 92. The near-infrared light may be transmitted from only the to-be-punctured portion in the front-side skin surface 23, so that the visualization of the to-be-punctured artery 21 becomes more reliable.

As fixtures 94 for fixing the visualization site 20 in the state of being pressed against the light guiding part 40, for example, surface fasteners 95a and 95b which are generally called Magic Tape (registered trademark) are installed at both ends of the light shielding member 90. The surface fastener 95a of the light shielding member 90 is detachably adhered to the surface fastener 95b of the chassis 31 side. By fixing the light shielding member 90 by using the fixture 94, the visualization site 20 is fixed in the state of being pressed against the light guiding part 40, so that it is possible to prevent the position of the light shielding member 90 from being shifted or deviated during the artery visualization. Accordingly, it is possible to more reliably perform the visualization of the to-be-punctured artery 21.

As described heretofore, the artery visualization device 10 according to the first embodiment has the following features.

(1) The light guiding part 40 is formed with a material which transmits the near-infrared light emitted from the light source 32 and suppresses the reflection of the near-infrared light on the surface of the back-side skin surface 22, the light source 32 is encapsulated by the light guiding part 40 and the light guiding part 40 is pressed against the back-side skin surface 22, so that the reflection of the near-infrared light does not occur on the surface of the back-side skin surface 22 which is the incidence side of the near-infrared light.

(2) The near-infrared light is incident on the artery running portion from the back-side skin surface 22, and the absorption image of the near-infrared light absorbed by the artery 21 is formed in the camera 60 which captures the image from the side of the front-side skin surface 23. Since the near-infrared light is incident on the back-side skin surface 22, the reflection of the near-infrared light does not occur on the surface of the front-side skin surface 23.

(3) By pressing the back-side skin surface 22 by using the light guiding part 40, the capillary network of the skin is collapsed, se that the absorption of the near-infrared light in the skin portion on which the near-infrared light is incident is suppressed.

Due to the above features, possible to very appropriately visualize the to-be-punctured artery 21.

Since the front-side skin surface 23 and the imaging unit 60 are arranged so as to be separated from each other and the work space 80 where the puncture is performed is installed between the front-side skin surface 23 and the imaging unit 60, it is possible to visualize the to-be-punctured artery 21 without interfering with puncturing manipulation procedures.

Since the pressing portion 42 which protrudes toward the back-side skin surface 22 to press the back-side skin surface 22 is formed in the light guiding part 40, the capillary network of the skin is easily collapsed by locally pressing the back-side skin surface 22 by using the pressing portion 42. Accordingly, it is possible to further suppress the absorption of the near-infrared light in the skin portion on which the near-infrared light is incident, so that it is possible to more clearly visualize the artery 21.

Since the light shielding member 90 which is configured to include the light shielding portion 91 and the observation window 92 to cover the front-side skin surface 23 is further installed, near-infrared, light may be transmitted from only the to-be-punctured portion in the front-side skin surface 23, so that the visualization of the to-be-punctured artery 21 becomes reliable.

By allowing the protruding portion 93 of the light shielding member 90 to be in contact with the front-side skin surface 23, the rear-infrared light may be transmitted from only the to-be-punctured portion in the front-side skin surface 23, so that the visualization of the to-be-punctured artery 21 becomes more reliable.

Since the irradiated near-infrared light is set to be in a wavelength range of 840 to 950 nm, it is possible to very appropriately visualize the artery 21 located at the position in the depth of 5 to 10 mm beneath the skin.

Since the material for forming the light guiding part 40 is the silicon rubber having a high transmittance with respect to the near-infrared light and a refractive index close to that of the living body and the refractive index is in a range of 1.33 to 1.44, it is possible to further suppress the reflection of the near-infrared light on the surface of the back-side skin surface 22.

By setting the pressure of pressing the light guiding part 40 against the back-side skin surface 22 to be in a range of 20 to 40 mmHg, the capillary network of the skin is collapsed by pressing the back-side skin surface 22, so that it is possible to suppress the absorption of the near-infrared light in the skin portion on which the near-infrared light is incident.

In the case where the artery for visualization is the radial artery 21 or the brachial artery, in the puncture operation which is performed for the purpose of the catheterization examination and the invasive arterial pressure measurement, it is possible to reliably and easily perform the puncture by visualizing the radial artery 21 or the brachial artery.

Second Embodiment

Figure 4:
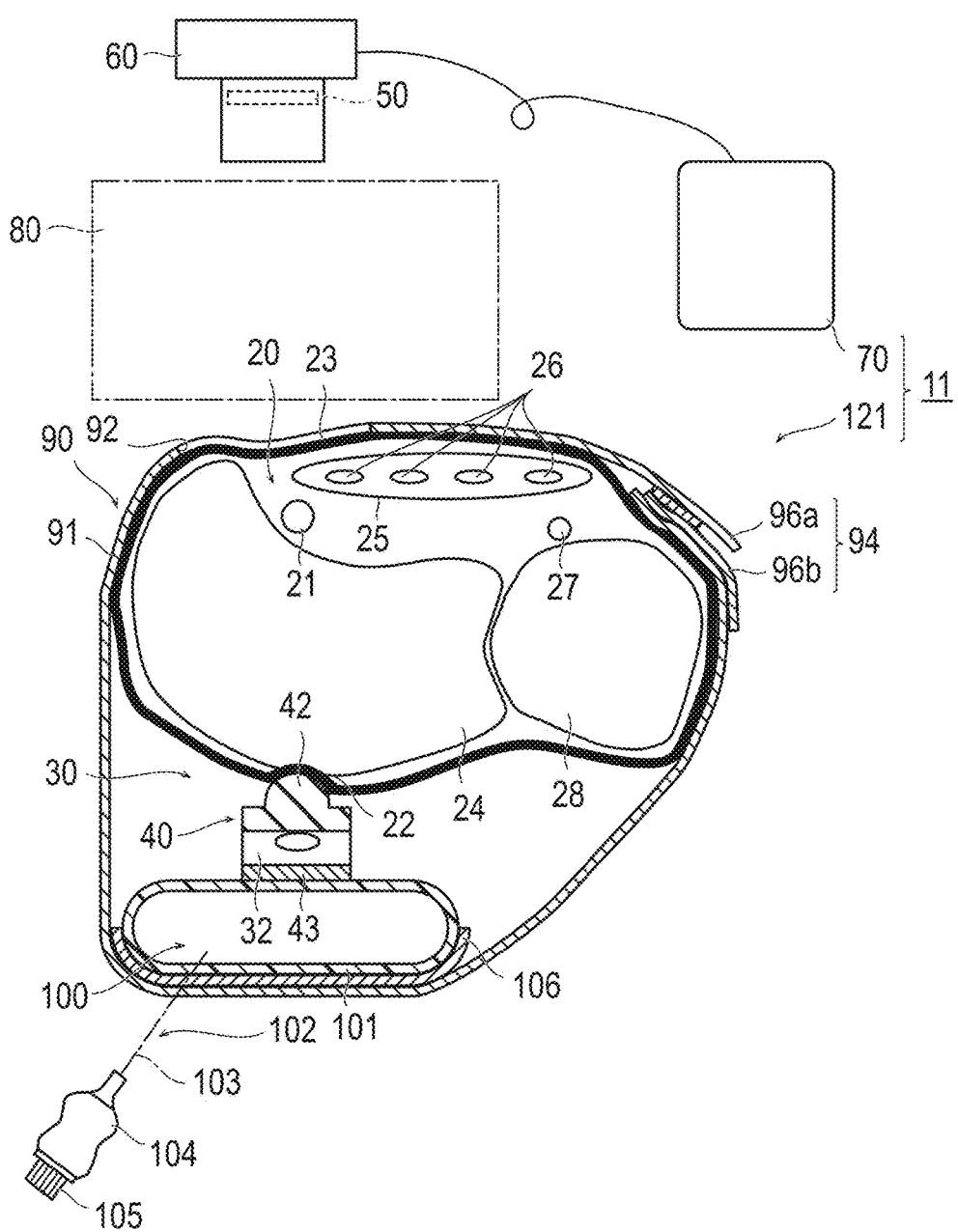
FIG. 4 is a cross-sectional diagram illustrating an artery visualization device according second embodiment.

FIG. 4 is a cross-sectional diagram illustrating an artery visualization device 11 according to a second embodiment. The same members as those of the first embodiment are denoted by the same reference numerals, and some of the description thereof is omitted.

Similarly to the first embodiment, the artery visualization device 11 according to the second embodiment is configured to include an irradiation unit 30 which irradiates near-infrared emitted from a light source 32 toward a back-side skin surface 22 at a visualization site 20, a light guiding part 40 which encapsulats the light source 32 and is pressed against the back-side skin surface 22, an optical filter 50, a camera 60, a monitor 70, a work space 80, and a light shielding member 90. However, the second embodiment is different from the first embodiment in that a pressure regulating unit 100 which is capable of regulating a pressure of pressing the light guiding part 40 against the back-side skin surface 22 is further included. In addition, the second embodiment is also different from the first embodiment in that the light shielding member 90 has a shape which is attachable by being wound around the visualization site 20.

A light-shielding portion 91 which is formed with a material of blocking the near-infrared light and is capable of being wound around the visualization site 20 and an observation window 92 opened for imaging the visualization site 20 are installed in the light shielding member 90 according to the second embodiment. The light shielding member 90 may be configured to cover a front-side skin surface 23 in the state that the observation window 92 is allowed to be located just over a radial artery 21 and to be further wound around the visualization site 20. By covering with the light shielding member 90, the near-infrared light may be transmitted from only the to-be-punctured portion in the front-side skin surface 23, so that the visualization of the to-be-punctured artery 21 becomes reliable. As a material of blocking the near-infrared light, for example, a light-shielding rubber may be exemplified, but not limited thereto.

As fixtures 94 for fixing the visualization site 20 in the state of being pressed against the light guiding part 40, for example, surface fasteners 96a and 96b are installed at both ends of the light shielding member 90. The surface fasteners include the first surface fastener 96a which is installed at the end portion of the back surface side of the light-shielding portion 91 and the second surface fastener 96b which is installed at the end portion of the front surface side to be detachably adhered to the first surface fastener 96a. By fixing the light shielding member 90 to be being wound around the visualization site 20 by using the fixtures 94, the visualization site 20 is fixed in the state of being pressed against the light guiding part 40, so that it is possible to prevent the position of the light shielding member 90 from being shifted or deviated during the artery visualization.

The pressure regulating unit 100 is configured to include a balloon 101 which is expanded by injecting a fluid and an injection unit 102 which injects the fluid into the balloon 101. Similarly to a cuff for blood pressure measurement, the balloon 101 is formed with an inflatable rubber material. The injection unit 102 is configured to include a hollow tube 103 which is connected to the balloon 101 and an air supply tool 104 which supplies air as the fluid to the balloon 101 through the hollow tube 103. A manipulator 105 which operates a valve (not shown) for regulating an air pressure of the balloon 101 is installed in the air supply tool 104. The light source 32 is attached on the outer surface of the balloon 101 so as to face the back-side skin surface 22. In the figure, reference numeral 106 denotes a holdplate 106 which is attached to the balloon 101 to hold the balloon 101. By pressing the holdplate 106 on a table or the like through the light shielding portion 91, it is possible to stabilize a posture of the visualization site 20 during the artery visualization.

In the case of regulating the pressure of pressing the light guiding part 40 against the back-side skin surface 22, the air pressure of the balloon 101 is regulated by the pressure regulating unit 100 while checking the contact pressure detected by the pressure sensor 43 which is displayed on the monitor 70. By using the pressure regulating unit 100, it is possible to simply and reliably regulate the pressure of pressing the light guiding part 40 against the back-side skin surface 22 in a desired range, for example, in the aforementioned range of 20 to 40 mmHg. By pressing the light guiding part 40 in a range of 20 to 40 mmHg, the back-side skin surface 22 is pressed to collapse the capillary network of the skin, so that so that the absorption of the near-infrared light in the skin portion on which the near-infrared light is incident is suppressed.

As described heretofore, the artery visualization device 11 according to the second embodiment obtains the same functions and effects as those of the artery visualization device 10 according to the first embodiment. In addition, since the artery visualization device 11 according to the second embodiment is configured to include and the pressure regulating unit 100 which is capable of regulating the pressure of pressing the light guiding part 40 against the back-side skin surface 22, it is possible to simply and reliably regulate the pressure of pressing the light guiding part 40 against the back-side skin surface 22.

In the first and second embodiments, the artery visualization devices 10 and 11 where the display unit 70 is connected to the artery imaging devices 120 and 121 configured to include the irradiation unit 30, the light guiding part 40, the optical filter 50, and the imaging unit 60 are illustrated. However, the artery imaging devices 120 and 121 may be connected to an existing display unit. In this case, by preparing only the artery imaging devices 120 and 121, the artery visualization device capable of very appropriately visualizing the to-be-punctured artery 21 may be configured, so that the artery imaging devices have advantages in terms of costs.

Experimental Example

A result of an experiment of visualizing the radial artery 21 by using the artery visualization device 11 illustrated in FIG. 4 will be described.

As the light source 32 of the irradiation unit 30, one LED (VSMY7850X1 produced by Vishay) having an emission center wavelength of 850 nm was used. A current of 1.75 volts and 720 mA was flowed into the LED. As a material of the light guiding part 40, a liquid silicon rubber (Shin-Etsu Silicone one-component RTV rubber "KE-441" produced by Shin-Etsu Chemical Co., Ltd.) was used. The refractive index of the liquid silicon rubber used is 1.4. The optical filter 50 which blocks components having a wavelength shorter than 840 nm was inserted between the imaging element and the lens of the camera 60. By regulating the air pressure of the balloon by using the pressure regulating unit 100, the pressure of pressing the pressing portion 42 of the light guiding part 40 against the back-side skin surface 22 was regulated to be 40 mmHg. The visualization target was the left radial artery 21 of a 50-year-old man.

The near-infrared light was transmitted from the distal forearm dorsal side, and the distal radial palmar surface side where the radial artery 21 was expected to be running was observed by the near-infrared high-sensitivity camera. The discrimination of the arteries 21 and the veins was performed according to existence and non-existence of vascular pulsation.

The position of the radial artery 21 was recognized by ultrasonic diagnostic equipment. The radial artery 21 was running in the depth of 7 mm beneath the skin.

Figure 5:
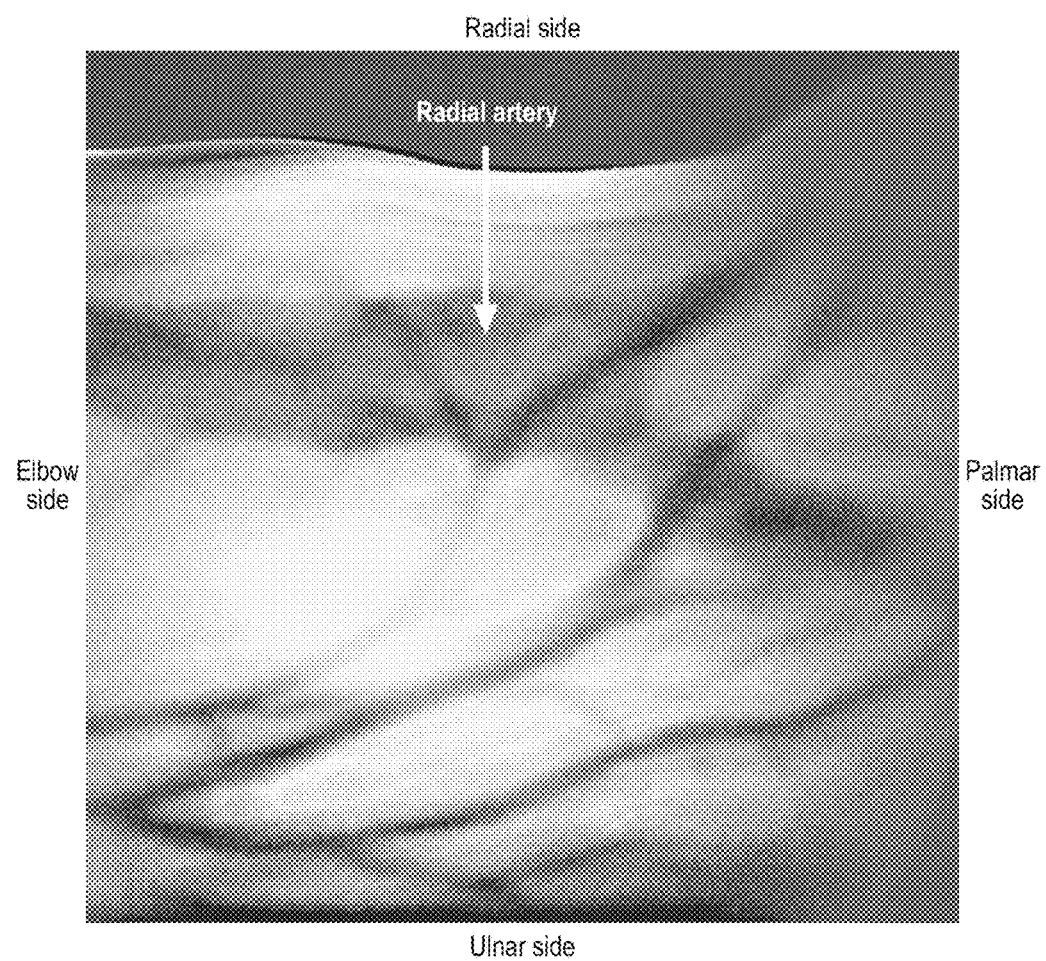
FIG. 5 is a diagram illustrating a transmission image obtained by an experiment where a radial artery is visualized by using the artery visualization device according to the second embodiment.

The obtained transmission image is illustrated in FIG. 5.

Visibility of a moving picture was identified. It the moving picture having 30 frames per second, since the artery pulsation is clear, the radial artery 21 is easy to identify. The running of the radial artery 21 observed by the ultrasonic diagnostic equipment and a planar image projected on the surface of the skin were completely identical to those that were visually recognized by using video data.

Comparative Example

Figure 6:
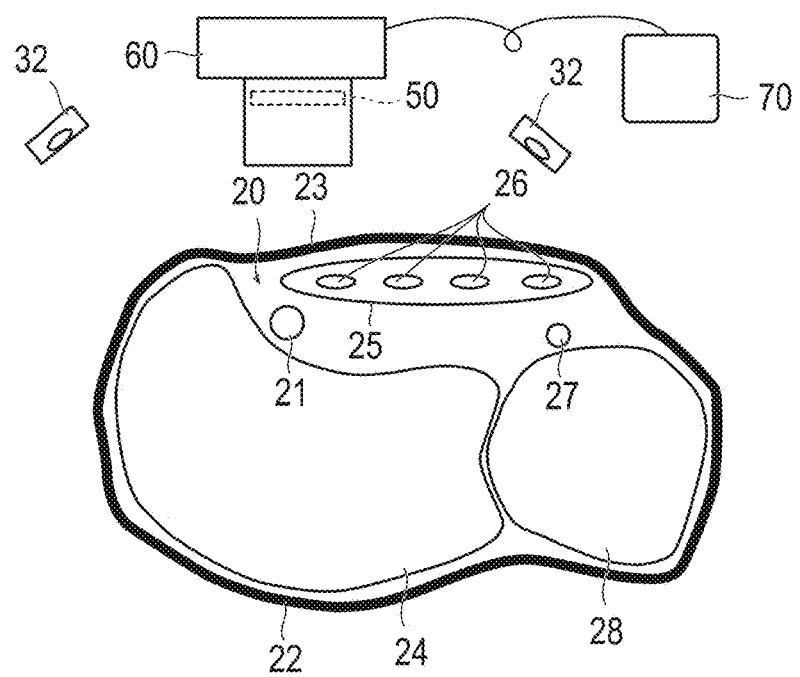
FIG. 6 is a cross-sectional diagram illustrating an artery visualization device according to Comparative Example.

FIG. 6 is a cross-sectional diagram illustrating an artery visualization device 10A according to Comparative Example.

Unlike the embodiments, in Comparative Example, the near-infrared light was irradiated toward the front-side skin surface 23 at the visualization site 20, that is, toward the skin surface of the side where the to-be-punctured portion exist. If the near-infrared light is irradiated toward the artery 21, the reflection light of which signal intensity is decreased due to the artery 21 may be obtained. Therefore, the projection image was tried to be obtained by generating the contrast due to the difference between the reflection light at the artery 21 and the reflection light at the peripheral tissues. The light source 32, the optical filter 50, and the camera 60 which were the same as those of the above-described Experimental Example were used.

Figure 7:
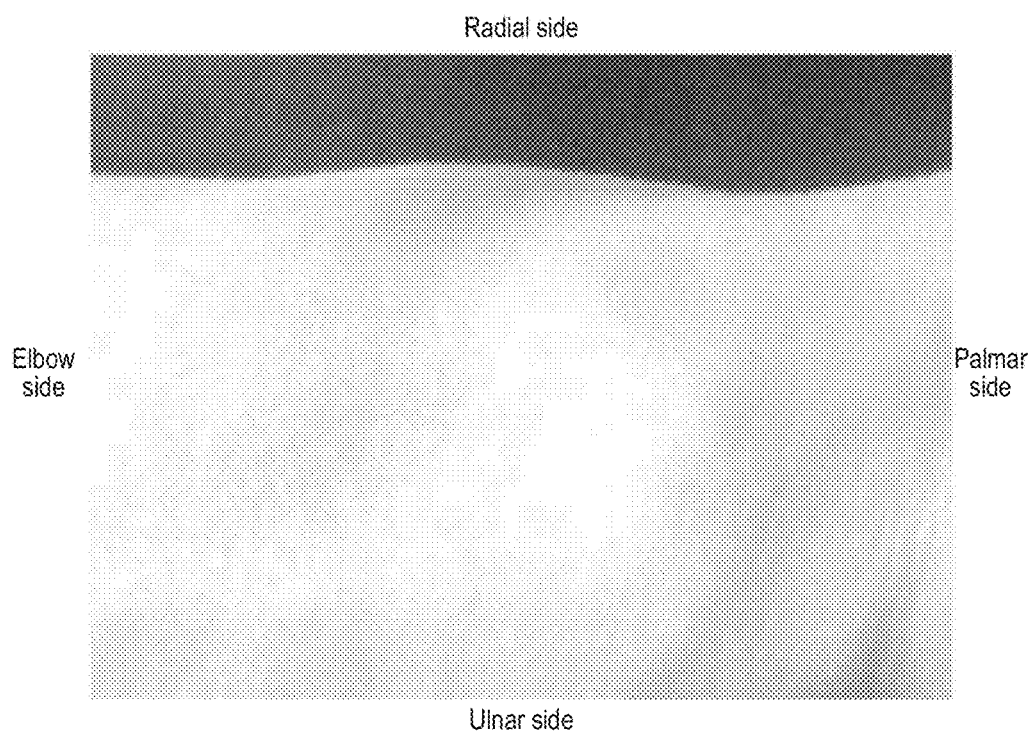
FIG. 7 is a diagram illustrating an image obtained by an experiment, where a radial artery is visualized by using the artery visualization device according to Comparative Example.

The obtained image is illustrated in FIG. 7.

As clarified from FIG. 7, only by observing the reflection light on the surface of the front-side skin surface 23, it was not possible to visualize the artery 21.

By replacing the light source 32, the wavelength of the near-infrared light is changed into a range of 750 to 950 nm, and the imaging was performed. However, since the reflectlection of the near-infrared light occurred on the skin surface, was not possible to visualize the artery 21.

This patent application is based on Japanese Patent Application No. 2012-121700, filed on May 29, 2012 in the Japan Patent Office, and the entire disclosure of which is hereby incorporated by reference herein.

REFERENCE SIGNS LIST 10, 11: Artery visualization device
20: Visualization site
21: Radial artery, to-be-punctured artery
22: Back-side skin surface
23: Front-side skin surface
24: Radius
27: Ulnar artery
28: Ulna
30: Irradiation unit
31: Chassis
32: Light source
40: Light guiding part
42: Pressing portion
43: Pressure sensor
50: Optical filter
60: Camera (imaging unit)
70: Monitor (display unit)
80: Work space
90: Light shielding member
91: Light shielding portion
92: Observation window
93: Protruding portion
94: Fixture
100: Pressure regulating unit
101: Balloon
102: Injection unit
120, 121: Artery imaging device

The invention claimed is:

1. An artery imaging device comprising:
   an irradiation unit which includes a light source emitting near-infrared light and irradiates the near-infrared light emitted from the light source toward a first skin surface of a body part at a visualization site where a to-be-punctured artery is running;
   a light guide, the light guide encapsulating the light source, the light guide including a pressing portion, the light guide formed with a material transmitting the near-infrared light emitted from the light source and suppressing reflection of the near-infrared light at the first skin surface, the pressing portion being in the form of a protrusion facing toward the first skin surface to press against the first skin surface, wherein the near-infrared light is irradiated toward the first skin surface through the protrusion;
   an optical filter which blocks visible light and transmits the near-infrared light passing through a second skin surface of the body part opposite the first skin surface at the visualization site; and
   an imaging unit configured to receive the near-infrared light passing through the optical fitter to capture an image of the visualization site; and
   a pressure sensor, the pressure sensor detecting the pressure of the protrusion against the first skin surface, the pressure sensor located on a back side of the light source and opposite the protrusion.

2. The artery imaging device according to claim 1, wherein the second skin surface and the imaging unit are arranged so as to be separated from each other, and a work space where puncture is performed exists between the second skin surface and the imaging unit.

3. The artery imaging device according to claim 1, further comprising a pressure regulating unit, the pressure regulating unit comprising an inflatable member, the inflatable member being positioned behind the pressure sensor and opposite the protrusion, whereby the pressure of the protrusion against the first skin surface can be regulated by the pressure in the inflatable member.

4. The artery imaging device according to claim 2, wherein the light shielding member is configured to include a protruding portion which is arranged around the observation window and protrudes from the light-shielding portion, and by allowing the protruding portion to be in contact with the second skin surface, the near-infrared light passing through a site excluding the site which faces the observation window in the second skin surface is blocked from being mixed into the observation window.

5. The artery imaging device according to claim 1, wherein the near-infrared light has a wavelength of 840 to 950 nm.

6. The artery imaging device according to claim 1, wherein a material for forming the light guiding part has a high near-infrared light transmittance and is a silicon rubber of which refractive index is close to that of a living body, and the refractive index is in a range of 1.33 to 1.44.

7. The artery imaging device according to claim 1, wherein a pressure for pressing the protrusion against the first skin surface is in a range of 20 to 40 mmHg.

8. The artery imaging device according to claim 1, wherein the to-be-visualized artery is a radial artery or a brachial artery.

9. An artery visualization device comprising the artery imaging device according to claim 1, further comprising a monitor which displays the image captured by the imaging unit.

10. The artery imaging device according to claim 2, further comprising a pressure regulating unit which is capable of regulating a pressure of pressing the light guiding part against the first skin surface.

11. The artery imaging device according to claim 2, further comprising a light shielding member configured for covering the second skin surface, the light shielding member including a light-shielding portion formed with a material of blocking the near-infrared light and an observation window opened for imaging the visualization site.

12. The artery imaging device according to claim 2, wherein the near-infrared light has a wavelength of 840 to 950 nm.

13. The artery imaging device according to claim 2, wherein a material for forming the light guide has a high near-infrared light transmittance and is a silicon rubber of which refractive index is close to that of a living body, and the refractive index is in a range of 1.33 to 1.44.

14. The artery imaging device according to claim 2, wherein a pressure for pressing the light guiding part against the first skin surface is in a range of 20 to 40 mmHg.

15. The artery imaging device according to claim 2, wherein the to-be-visualized artery is a radial artery or a brachial artery.

16. An artery visualization device comprising the artery imaging device according to claim 2, further comprising a monitor which displays the image captured by the imaging unit.

17. The artery imaging device according to claim 1, further comprising a light shielding member configured for covering the second skin surface, the light shielding member including a light-shielding portion formed with a material for blocking the near-infrared light and an observation window opened for imaging the visualization site.

18. The artery imaging device according to claim 11, wherein the light shielding member is configured to include a protruding portion which is arranged around the observation window and protrudes from the light-shielding portion, and by allowing the protruding portion to be in contact with the second skin surface, the near-infrared light passing through a site excluding the site which faces the observation window in the second skin surface is blocked from being mixed into the observation window.

* * * * *